United States Patent [19]
Carodiskey

[11] 4,368,642
[45] Jan. 18, 1983

[54] ULTRASONIC TRANSDUCER PROBE

[75] Inventor: Thomas J. Carodiskey, McVeytown, Pa.

[73] Assignee: Krautkramer-Branson, Inc., Stratford, Conn.

[21] Appl. No.: 236,888

[22] Filed: Feb. 23, 1981

[51] Int. Cl.³ ............................................ G01N 29/04
[52] U.S. Cl. ...................................... 73/623; 73/633; 73/634
[58] Field of Search .......................... 73/623, 633, 634

[56] References Cited

U.S. PATENT DOCUMENTS

| | | | |
|---|---|---|---|
| 4,194,400 | 3/1980 | Staff | 73/623 |
| 4,241,609 | 12/1980 | Bergman et al. | 73/623 |
| 4,306,459 | 12/1981 | Johnson et al. | 73/623 |

FOREIGN PATENT DOCUMENTS

| | | | |
|---|---|---|---|
| 2547472 | 4/1977 | Fed. Rep. of Germany | 73/623 |
| 508736 | 12/1976 | U.S.S.R. | 73/634 |

*Primary Examiner*—Anthony V. Ciarlante
*Attorney, Agent, or Firm*—Ervin B. Steinberg; Philip J. Feig

[57] ABSTRACT

An ultrasonic transducer probe for testing workpieces exhibiting compound surfaces includes a molded plastic body which precisely fits to the shape of such workpiece surfaces. Moreover, the body includes, as an integral part thereof, an indexing portion for accurately locating the transducer probe in relation to a predetermined workpiece test area to cause the transducer element embedded in the molded body to transmit ultrasonic energy in the predetermined test area. The transducer probe is secured to a manipulator for remote operation.

7 Claims, 5 Drawing Figures

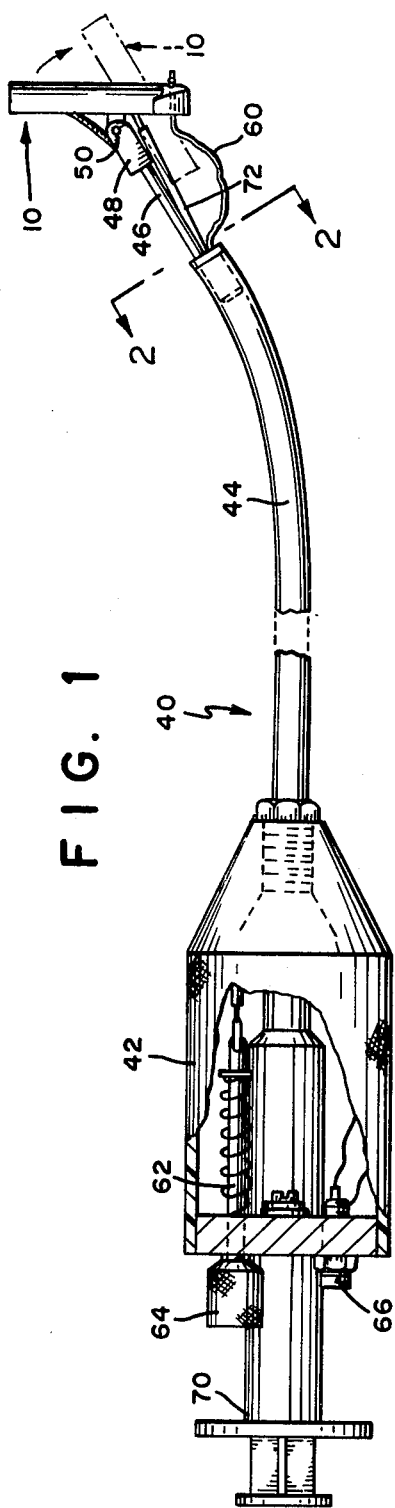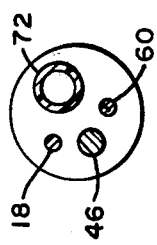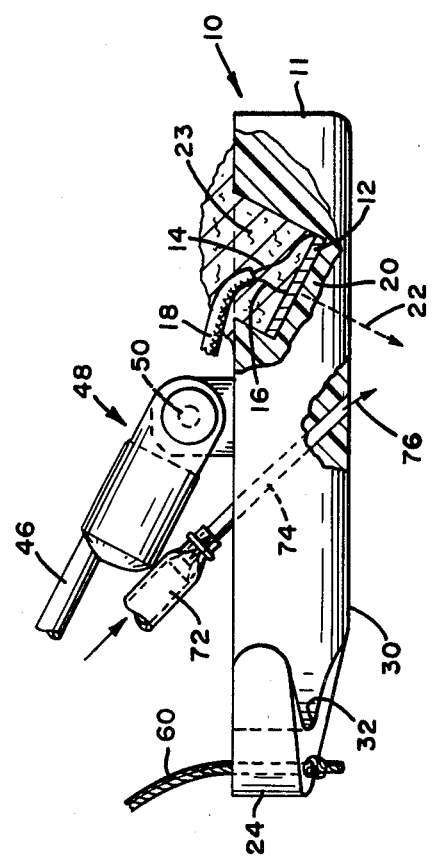

ULTRASONIC TRANSDUCER PROBE

SUMMARY OF THE INVENTION

This invention relates to testing workpieces by acoustic waves and more specifically refers to an ultrasonic transducer probe for transmitting ultrasonic search signals into a workpiece and for receiving ultrasonic echo signals arising from a change in acoustic impedance encountered by the search signals. Quite specifically, this invention refers to an ultrasonic transducer probe which comprises a molded body and is adapted by means of an indexing portion to be located most precisely in relation to a predetermined workpiece area to be tested by the pulse-echo ultrasonic test method.

Testing of critical components by ultrasonic energy is well established in the art. Frequently, workpieces or components exhibiting a complex surface contour must be tested. Such complex contours represent considerable difficulties. One technique of testing parts having complex contours involves the so-called water immersion test method. This method comprises immersing the complex part in a liquid bath, such as water, and then coupling ultrasonic energy through the water path to the workpiece surface. This method is possible only if the workpiece to be tested is readily available as an individual part and adapted to be immersed in a water bath.

The present application concerns the testing, for instance, of turbine blades on a rotor, including the testing when such blades and rotor are in situ, as may be the case in an airplane engine. In such a case inspection must be performed on an assembly with limited accessibility and it is necessary that a small transducer be inserted through a narrow aperture into a complicated turbine rotor assembly and positioned with utmost precision on a turbine blade in order to test the root of the blade for defects, such as cracks. Testing of components of this type presents unique problems and it is obvious that the degree of confidence with which such testing can be accomplished is most critical.

The present invention discloses a transducer assembly which is adapted to be manipulated with great ease and which can be positioned for contacting a complicated workpiece, such as a turbine blade, with utmost precision in order to obtain reliable and accurate test data. Accurate positioning of the transducer is obtained despite the fact that there exists limited visibility of the test area.

One of the principal objects of this invention is therefore the provision of a new and improved transducer probe construction for testing workpieces exhibiting intricate surface contours.

Another important object of this invention is the provision of a transducer probe which comprises a molded body having an indexing portion as a part of the molded body in order to enable an operator to accurately locate the transducer probe in predetermined relation relative to the workpiece area to be tested.

Further and other objects of this invention will be more clearly apparent by reference to the following description when taken in conjunction with the accompanying drawings.

BRIEF DESCRIPTION OF THE DRAWINGS

FIG. 1 is a side view, partly in section, of the transducer probe assembly with manipulator;

FIG. 2 is a sectional view along line 2—2 in FIG. 1;

FIG. 3 is a side view, partially in section, of the transducer probe;

DETAILED DESCRIPTION OF THE INVENTION

Figure 4:
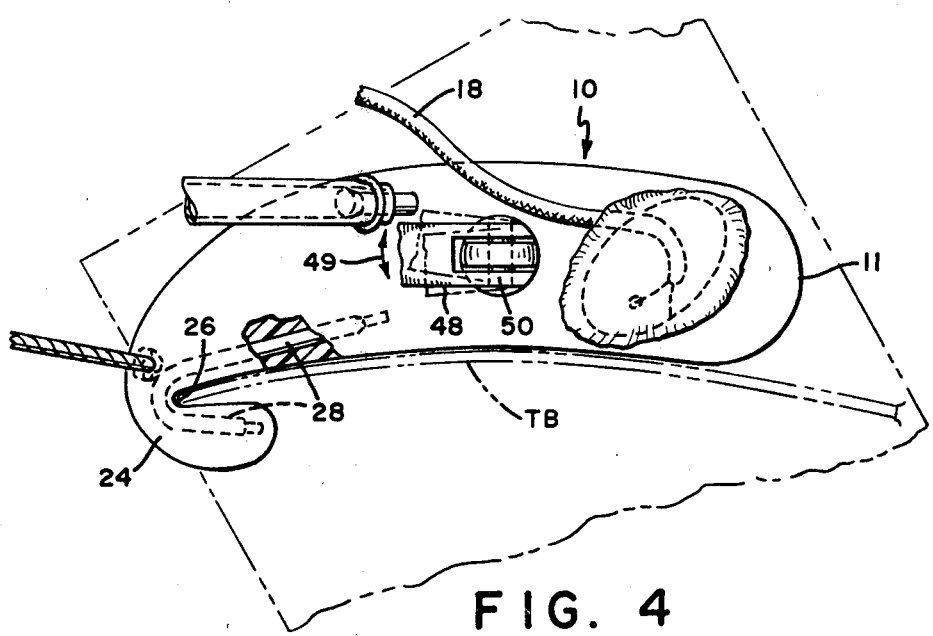
FIG. 4 is a top view, partly in section, of the transducer probe disposed in contact with a turbine blade.

Referring now to the figures and FIGS. 3 and 4 in particular, there is shown a transducer probe 10 comprising an elongated molded body 11 which includes imbedded therein a piezoelectric element 12 adapted to be energized with high frequency electrical energy by means of electrical conductors 14 and 16 forming a cable 18. The molded body 11 typically comprises suitable epoxy material and it will be noted that the piezoelectric element 12 (transducer) is recessed in order that the molded plastic material 20 in front of the piezoelectric element 12 forms a so-called ultrasonic delay line for the ultrasonic energy before the ultrasonic energy enters the workpiece surface. The delay line permits near-surface inspection as is well known to those skilled in the art. Moreover, the piezoelectric element 12 is so positioned within the molded body that the ultrasonic energy is transmitted along a predetermined beam axis 22 into the workpiece area to be tested. Damping material 23, the well known mixture of tungsten powder and epoxy, is disposed within the molded body to the rear of the piezoelectric element 12 in order to provide the required mechanical damping of the piezoelectric element.

Importantly, the molded body 11 includes an indexing portion 24 which, as more clearly seen in FIG. 4, is a return portion to snugly fit around the left edge 26 of the turbine blade TB. This return portion 24, hook shaped, is reinforced by an imbedded wire 28 in order to prevent this return portion from breaking off.

Figure 5:
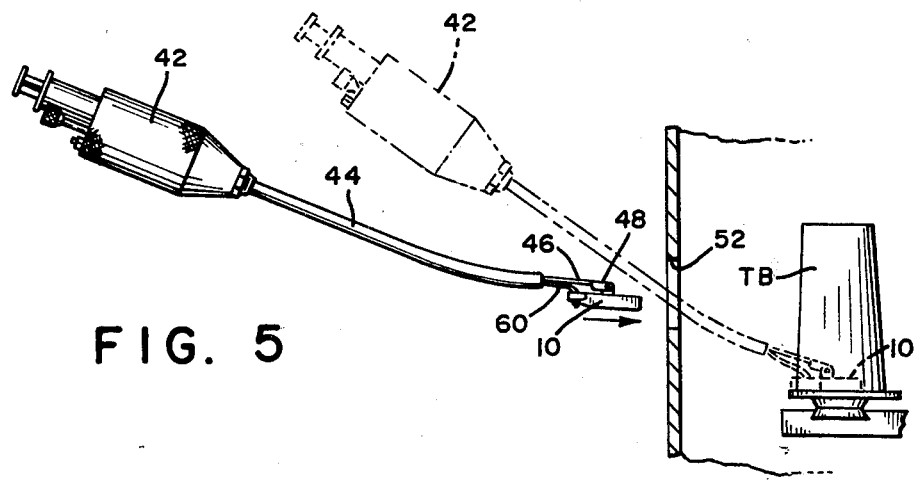
FIG. 5 is a view showing how the transducer probe assembly is manipulated through an aperture for contact with a turbine blade.

The workpiece engaging surface or surfaces 30 of the ultrasonic transducer probe in connection with the return 24 and the inside contour 32 of the molded body 11 are so configured as to precisely conform to the blade construction TB, FIG. 5, at the root of the blade TB in order to accurately transmit ultrasonic energy into the critical root area. Importantly also, the transducer body with its return portion, which serves for accurately indexing the transducer probe, form a unitary body which is precisely molded with the piezoelectric element 12 accurately positioned within the unitary body. In practice, the body 11 may be molded by special moulds which have been made by impressions taken of the actual workpiece.

In order to manipulate the transducer body from a distant location, the molded transducer probe body is mounted to a manipulator 40 which comprises a hand grip 42 from which extends a substantially rigid tubing 44 and a substantially rigid wire 46. The transducer probe is pivotally mounted to the wire 46 and tubing 44 by means of a pivoting mechanism generally identified by numeral 48 which includes a pivoting pin 50 extending through a bifurcated bracket mounted to the wire 46. In order to enable proper positioning, the transducer body not only is capable of pivoting about the pin 50 but there is also provided a lateral play so that the transducer body becomes self-aligning against the workpiece surface when engagement pressure is applied to the probe 10 via the hand grip 42, tubing 44, wire 46 and the pivotal mounting means 48.

In order to insert the probe through a relatively small opening 52, see FIG. 5, there is provided a pull mechanism for causing the probe to rotate about pin 50 and become generally aligned with the wire 46, see FIG. 5, solid lines. The pull mechanism comprises a flexible wire 60 attached to the molded probe body at its return portion 24 and this flexible wire 60, in turn, is connected to a pull mechanism 62 which includes the knob 64 of the handgrip 42. Thus it can be seen, with reference to FIG. 5, that upon pulling the knob 64 the wire 60 becomes taut and rotates the probe 10 to facilitate its insertion through a limited access aperture 52 into the workpiece area. In addition, the handgrip 42 contains an electrical connector 66 which is the terminal for the electrical conductor 18 providing electrical energy to the piezoelectric element 12 and receiving the echo responsive electrical signals.

In order to provide a liquid couplant medium, such as water, into the contact area between the transducer body and the workpiece, there is provided a metering device 70 in the form of a syringe for discharging liquid couplant through a flexible hose 72 which discharges the liquid couplant through an inclined passage 74 of the molded probe body into the contact area between the transducer probe and the workpiece TB. The discharge of couplant liquid is indicated by arrow 76, FIG. 3.

It will be seen therefore that the present invention deals with a transducer probe arrangement which is adapted to be fed through a narrow space and placed in contact with a workpiece exhibiting a complex surface contour. The transducer body is molded to conform precisely to such complex contour and, moreover, includes as an integral part of its construction an indexing portion which accurately permits the placing of the transducer body in predetermined relation with the workpiece for causing ultrasonic waves to be propagated into a predetermined test area. Additionally, the indexing means which forms a part of the transducer body permits the accurate placement of the transducer probe and such placement can be felt at the manipulator by virtue of the rigid mechanical connection between the probe and the manipulator. The accurate positioning of the probe, aside from the precise contour of the molded transducer body, is assured by the pivoting arrangement 48, 50 which includes a limited amount of lateral play as is indicated by the arrow 49 in FIG. 4.

While there has been described and illustrated a preferred embodiment of the present invention it will be apparent to those skilled in the art that various changes and modifications may be made therein without deviating from the broad principle of the invention which shall be limited only by the scope of the appended claims.

What is claimed is:

1. An ultrasonic transducer probe assembly comprising:
    an elongated molded transducer body shaped externally to conform with a workpiece engaging surface to the contour of a workpiece area to be tested and including as an integral part of the molded body a hook shaped indexing portion for locating said workpiece engaging surface in a predetermined position relative to said workpiece area, and
    a piezoelectric transducer means enclosed within said molded body and positioned rearwardly of said workpiece engaging surface and oriented to transmit ultrasonic energy toward a predetermined workpiece portion when said workpiece engaging surface is in said predetermined position whereby the molded body material disposed between said piezoelectric means and said workpiece engaging surface acts as a delay for the ultrasonic signals traversing the distance between said piezoelectric means and the workpiece.

2. An ultrasonic transducer probe assembly as set forth in claim 1, and pivoting means fastening said transducer body to a manipulator.

3. An ultrasonic transducer probe assembly as set forth in claim 1, said hook shaped indexing portion enveloping the edge of a workpiece.

4. An ultrasonic transducer probe assembly comprising:
    an elongated molded transducer body shaped externally to conform with a workpiece engaging surface to the contour of a workpiece area to be tested and including as a part of the molded body a hook shaped indexing portion for locating said workpiece engaging surface in a predetermined position relative to said workpiece area;
    a piezoelectric transducer means enclosed within said molded body and positioned rearwardly of said workpiece engaging surface and oriented to transmit ultrasonic energy toward a predetermined workpiece portion when said workpiece engaging surface is in said predetermined position whereby the molded body material disposed between said piezoelectric means and said workpiece engaging surface acts as a delay for the ultrasonic signals traversing the distance between said piezoelectric means and the workpiece;
    a manipulator;
    means for movably fastening said transducer body to one end of said manipulator;
    a grip at the other end of said manipulator;
    electrical circuit connections extending from said piezoelectric element to said grip;
    flexible pull means disposed between said grip and one end of said body for imparting a limited pivotal motion to said body;
    a metering device for dispensing a liquid couplant disposed on said grip, and
    liquid conducting means extending from said metering device along said manipulator and coupled to said body for providing such couplant to the contact area between the workpiece engaging surface of said body and the workpiece.

5. An ultrasonic transducer probe as set forth in claim 4, said transducer body having a passage therethrough which is coupled to said liquid conducting means for flowing couplant into said contact area.

6. An ultrasonic transducer probe set forth in claim 4, said hook-shaped indexing portion being a unitary part of said molded body and including reinforcing means.

7. An ultrasonic transducer probe set forth in claim 4, said means for movably supporting said transducer including a pivotal mount providing motion of said body about the pivotal axis as well as limited lateral motion relative to said axis.

* * * * *